US010238773B2

United States Patent
Li et al.

(10) Patent No.: US 10,238,773 B2
(45) Date of Patent: *Mar. 26, 2019

(54) METHODS OF MAKING COLLAGEN FIBER MEDICAL CONSTRUCTS AND RELATED MEDICAL CONSTRUCTS, INCLUDING NERVE GUIDES AND PATCHES

(71) Applicant: MiMedx Group, Inc., Marietta, GA (US)

(72) Inventors: Mengyan Li, Tampa, FL (US); Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 712 days.

This patent is subject to a terminal disclaimer.

(21) Appl. No.: 14/734,548

(22) Filed: Jun. 9, 2015

(65) Prior Publication Data

US 2015/0283305 A1    Oct. 8, 2015

Related U.S. Application Data

(62) Division of application No. 12/576,435, filed on Oct. 9, 2009, now Pat. No. 9,078,775.

(Continued)

(51) Int. Cl.
*A61L 31/04*    (2006.01)
*A61L 27/46*    (2006.01)
(Continued)

(52) U.S. Cl.
CPC .......... *A61L 27/46* (2013.01); *A61B 17/1128* (2013.01); *A61B 17/1146* (2013.01);
(Continued)

(58) Field of Classification Search
CPC .......... A61B 17/0401; A61B 17/06166; A61B 17/1128; A61B 17/1146; A61B 2050/314; A61B 50/30; A61B 2017/00526; A61L 15/325; A61L 27/24; A61L 27/58; A61L 27/26; A61L 2430/10; A61L 27/50; A61L 31/044; A61L 27/507; A61L 57/56;
(Continued)

(56) References Cited

U.S. PATENT DOCUMENTS 3,316,699 A    5/1967   Mattingly
3,700,489 A *  10/1972  Borysko ............. D06M 15/256
                                                   427/2.28
(Continued)

FOREIGN PATENT DOCUMENTS

CA    2285161    4/2001
EP    1319415    6/2003
(Continued)

OTHER PUBLICATIONS

Brunelli et al., Slip-knot flexor tendon suture in zone II allowing immediate mobilisation, The Hand, 1983, vol. 15, pp. 352-358.
(Continued)

*Primary Examiner* — Vishal I Patel
(74) *Attorney, Agent, or Firm* — Myers Bigel, P.A.

(57) ABSTRACT

The disclosure describes methods of winding collagen fiber to make medical constructs and related collagen fiber tube and patch devices.

33 Claims, 10 Drawing Sheets

Related U.S. Application Data

(60) Provisional application No. 61/103,995, filed on Oct. 9, 2008, provisional application No. 61/138,165, filed on Dec. 17, 2008.

(51) Int. Cl.

| | | |
|---|---|---|
| *A61F 2/06* | (2013.01) | |
| *A61B 17/11* | (2006.01) | |
| *A61L 15/32* | (2006.01) | |
| *A61L 27/24* | (2006.01) | |
| *A61L 27/58* | (2006.01) | |
| *A61F 2/82* | (2013.01) | |
| *B32B 37/14* | (2006.01) | |
| *B32B 37/20* | (2006.01) | |
| *B32B 38/08* | (2006.01) | |
| *A61B 50/30* | (2016.01) | |
| *A61F 2/04* | (2013.01) | |
| *A61L 27/26* | (2006.01) | |
| *A61L 27/50* | (2006.01) | |
| *A61L 27/56* | (2006.01) | |
| *A61L 27/34* | (2006.01) | |
| *A61B 17/04* | (2006.01) | |
| *A61B 17/06* | (2006.01) | |
| *B29C 53/58* | (2006.01) | |
| *B29C 53/66* | (2006.01) | |
| *A61B 17/00* | (2006.01) | |

(52) U.S. Cl.
CPC ............... *A61B 50/30* (2016.02); *A61F 2/04* (2013.01); *A61F 2/06* (2013.01); *A61F 2/82* (2013.01); *A61L 15/325* (2013.01); *A61L 27/24* (2013.01); *A61L 27/26* (2013.01); *A61L 27/34* (2013.01); *A61L 27/507* (2013.01); *A61L 27/56* (2013.01); *A61L 27/58* (2013.01); *A61L 31/044* (2013.01); *B32B 37/142* (2013.01); *B32B 37/20* (2013.01); *B32B 38/08* (2013.01); *A61B 17/0401* (2013.01); *A61B 17/06166* (2013.01); *A61B 2017/00526* (2013.01); *A61B 2050/314* (2016.02); *A61F 2210/0004* (2013.01); *A61F 2210/0076* (2013.01); *A61F 2230/0067* (2013.01); *A61F 2230/0069* (2013.01); *A61F 2240/00* (2013.01); *A61F 2240/001* (2013.01); *A61L 27/50* (2013.01); *A61L 2420/04* (2013.01); *A61L 2420/08* (2013.01); *A61L 2430/10* (2013.01); *A61L 2430/32* (2013.01); *B29C 53/58* (2013.01); *B29C 53/66* (2013.01); *B32B 2535/00* (2013.01)

(58) Field of Classification Search
CPC .. A61L 2430/32; A61L 27/46; A61L 2420/04; A61L 27/34; A61L 2420/08; B29C 53/58; B29C 53/66; A61F 2/82; A61F 2/06; A61F 2240/001; A61F 2230/0069; A61F 2230/0067; A61F 2/04; A61F 2210/0004; A61F 2240/00; A61F 2210/0076; B32B 38/08; B32B 37/20; B32B 37/142; B32B 2535/00; C08L 89/06
See application file for complete search history.

(56) References Cited

U.S. PATENT DOCUMENTS

| | | | |
|---|---|---|---|
| 3,791,388 A * | 2/1974 | Hunter | ............... A61L 17/145 264/186 |
| 4,590,928 A | 5/1986 | Hunt et al. | |
| 4,778,467 A | 10/1988 | Stensaas et al. | |
| 4,792,336 A | 12/1988 | Hlavacek et al. | |
| 4,841,962 A | 6/1989 | Berg et al. | |
| 4,883,486 A | 11/1989 | Kapadia et al. | |
| 4,923,380 A | 5/1990 | Huc et al. | |
| 4,979,956 A | 12/1990 | Silvestrini | |
| 5,028,695 A | 7/1991 | Eckmayer et al. | |
| 5,078,744 A | 1/1992 | Chvapil | |
| 5,106,949 A | 4/1992 | Kemp et al. | |
| 5,162,430 A | 11/1992 | Rhee et al. | |
| 5,256,418 A | 10/1993 | Kemp et al. | |
| 5,263,984 A | 11/1993 | Li et al. | |
| 5,378,469 A * | 1/1995 | Kemp | ............... A61L 27/24 424/423 |
| 5,569,302 A | 10/1996 | Proto et al. | |
| 5,656,605 A | 8/1997 | Hansson et al. | |
| 5,713,374 A | 2/1998 | Pachence et al. | |
| 5,718,012 A | 2/1998 | Cavallaro | |
| 5,718,717 A | 2/1998 | Bonutti | |
| 6,090,117 A | 7/2000 | Shimizu | |
| 6,224,630 B1 | 5/2001 | Bao et al. | |
| 6,277,397 B1 | 8/2001 | Shimizu | |
| 6,280,474 B1 | 8/2001 | Cassidy et al. | |
| 6,292,697 B1 | 9/2001 | Roberts | |
| 6,335,007 B1 | 1/2002 | Shimizu et al. | |
| 6,420,625 B1 | 7/2002 | Jones et al. | |
| 6,514,286 B1 | 2/2003 | Leatherbury et al. | |
| 6,531,147 B2 | 3/2003 | Sawhney et al. | |
| 6,565,960 B2 | 5/2003 | Koob et al. | |
| 6,589,257 B1 | 7/2003 | Shimizu | |
| 6,592,623 B1 | 7/2003 | Bowlin et al. | |
| 6,596,296 B1 | 7/2003 | Nelson et al. | |
| 6,645,247 B2 | 11/2003 | Ferree | |
| 6,692,528 B2 | 2/2004 | Ward et al. | |
| 6,713,537 B1 | 3/2004 | Ueda et al. | |
| 6,730,124 B2 | 5/2004 | Steiner | |
| 6,752,831 B2 | 6/2004 | Sybert et al. | |
| 6,821,530 B2 | 11/2004 | Koob et al. | |
| 6,866,681 B2 | 3/2005 | Laboureau et al. | |
| 6,936,072 B2 | 8/2005 | Lambrecht et al. | |
| 6,953,482 B2 | 10/2005 | Doi et al. | |
| 6,955,683 B2 | 10/2005 | Bonutti | |
| 6,977,231 B1 | 12/2005 | Matsuda | |
| 7,048,963 B2 | 5/2006 | Braithwaite et al. | |
| 7,084,082 B1 | 8/2006 | Shimizu | |
| 7,090,690 B2 | 8/2006 | Foerster et al. | |
| 7,105,021 B2 | 9/2006 | Edens et al. | |
| 7,115,146 B2 | 10/2006 | Boyer et al. | |
| 7,135,040 B2 | 11/2006 | Wang et al. | |
| 7,264,859 B2 | 9/2007 | Rouns et al. | |
| 7,309,359 B2 | 12/2007 | Trieu et al. | |
| 7,354,627 B2 | 4/2008 | Pedrozo et al. | |
| 7,650,742 B2 | 1/2010 | Ushijima | |
| 8,367,148 B2 * | 2/2013 | Greenhalgh | ............ A61L 27/46 264/291 |
| 9,176,976 B2 * | 11/2015 | Koifman | ............... G06F 3/0623 |
| 2001/0018619 A1 | 8/2001 | Enzerink et al. | |
| 2002/0037940 A1 | 3/2002 | Koob et al. | |
| 2002/0123805 A1 | 8/2002 | Murray et al. | |
| 2002/0127270 A1 * | 9/2002 | Li | ............... A61L 27/24 424/443 |
| 2003/0003157 A1 | 1/2003 | Ohan et al. | |
| 2003/0100108 A1 | 5/2003 | Altman et al. | |
| 2003/0211130 A1 | 11/2003 | Sanders et al. | |
| 2003/0230316 A1 | 12/2003 | Glucksman et al. | |
| 2004/0110439 A1 | 6/2004 | Chaikof et al. | |
| 2004/0131562 A1 | 7/2004 | Gower et al. | |
| 2004/0193241 A1 | 9/2004 | Stinson | |
| 2004/0224406 A1 | 11/2004 | Altman et al. | |
| 2004/0267362 A1 | 12/2004 | Hwang et al. | |
| 2005/0009178 A1 | 1/2005 | Yost et al. | |
| 2006/0095134 A1 | 5/2006 | Trieu et al. | |
| 2006/0100647 A1 | 5/2006 | Doi et al. | |
| 2006/0200250 A1 | 9/2006 | Ku | |
| 2006/0257377 A1 | 11/2006 | Atala et al. | |
| 2006/0263417 A1 | 11/2006 | Lelkes et al. | |
| 2007/0020383 A1 * | 1/2007 | Matsuda | ............ A61B 17/06166 427/2.31 |
| 2007/0038290 A1 | 2/2007 | Huang et al. | |
| 2007/0118217 A1 | 5/2007 | Brulez et al. | |

(56) References Cited

U.S. PATENT DOCUMENTS

| | | | |
|---|---|---|---|
| 2007/0248643 A1 | 10/2007 | Devore et al. | |
| 2007/0269481 A1 | 11/2007 | Li et al. | |
| 2008/0020012 A1* | 1/2008 | Ju | A61L 27/24 424/423 |
| 2008/0038352 A1 | 2/2008 | Simpson et al. | |
| 2008/0124371 A1 | 5/2008 | Turos et al. | |
| 2008/0161917 A1 | 7/2008 | Koob et al. | |
| 2008/0188933 A1 | 8/2008 | Koob et al. | |
| 2008/0199506 A1 | 8/2008 | Horres et al. | |
| 2008/0200992 A1 | 8/2008 | Koob et al. | |
| 2008/0215150 A1 | 9/2008 | Koob et al. | |
| 2008/0286332 A1 | 11/2008 | Pacetti | |
| 2008/0300683 A1 | 12/2008 | Altman et al. | |
| 2009/0216233 A1 | 8/2009 | Wiedrich et al. | |
| 2009/0287308 A1 | 11/2009 | Davis et al. | |
| 2010/0076462 A1 | 3/2010 | Bakos et al. | |

FOREIGN PATENT DOCUMENTS

| | | |
|---|---|---|
| EP | 1493404 | 1/2005 |
| WO | WO 96/014095 | 5/1996 |
| WO | WO 01/15754 | 3/2001 |
| WO | WO 01/072241 | 10/2001 |
| WO | WO 08/033505 | 3/2008 |
| WO | WO 08/041183 | 4/2008 |
| WO | WO 08/093342 | 8/2008 |

OTHER PUBLICATIONS

Becker et al., Early active motion following a beveled technique of flexor tendon repair: Report on fifty cases, Journal of Hand Surgery, 1979, vol. 4 No. 5, pp. 454-460.

Greis et al, The influence of tendon length and fit on the strength of the tendon-bone tunnel complex, Am. J. Sports Med., 2001, 29:493-497.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

International Search Report and Written Opinion for related PCT application No. PCT/US2009/005542, dated May 17, 2010.

Koob et al., Biomimetic approaches to tendon repair, Comp. Biochem. Physiol. A Mol. Integr. Phys., 2002, 133: 1171-1192.

Koob et al., Material properties of NDGA-collagen composite fibers: development of biologically based tendon constructs, Biomaterials, 2002, 23:202-212.

Koob et al., Mechanical and thermal properties of novel polymerized NDGA-gelatin hydrogels, Biomaterials, 2002, 24:1285-1292.

Koob et al., Biocompatibility of NDGA-polymerized collagen fibers. I. Evaluation of cytotoxicity with tendon fibroblasts in vitro, © 2001John Wiley & Sons, Inc.

Koob et al., Biocompatibility of NDGA-polymerized collagen fibers. II. Attachment, proliferation, and migration of tendon fibroblasts in vitro, © 2001John Wiley & Sons, Inc.

Martin et al., Anterior Cruciate Ligament Graft Preparation: A New and Quick Alternative to the Whipstitch, Arthroscopy: The Journal of Arthroscopic & Related Surgery, Online Publication Date of Nov. 29, 2006.

Messina, The double armed suture: Tendon repair with immediate mobilization of the fingers, Journal of Hand Surgery, 1992, 17A:137-142.

Nottage et al., Arthoscopic Knot Tying Techniques, Arthroscopy: The Journal of Arthroscopic & Related Surgery 15(1999): 515-521.

Powell et al., Forces transmitted along human flexor tendons during passive and active movements of the fingers, J. Hand Surg., 2004, 29:4:386-389.

Rodeo et al., Tendon healing in a bone tunnel. A biomechanical and histological study in a dog, J. Bone Joint Surg., 1993, 75:1795-1803.

Savage et al., Flexor tendon repair using a "six strand" method of repair and early active mobilisation, Journal of Hand Surgery, (British Volume, 1989), 14B:396-399.

Silva et al., The insertion site of the canine flexor digitorum profundus tendon heals slowly following injury and suture repair, J. Orthop. Res., 2002, 20:447-453.

Trotter et al., Molecular structure and functional morphology of echinoderm collagen fibrils, Cell Tiss. Res., 1994, 275: 451-458.

Product advertisement, Conair QB3ECS Quick Braid Styling Kit, © 2007 (1 page).

Integra™ NeuraGen™ Nerve Guide, Product Brochure, 4 pages 2005.

Integra™ NeuraGen™ Nerve Guide, Product Webpage, http://www.integra-ls.com/products/?product=88, Date unknown but believed to be prior to the filing date of the present application, 2 pages.

Integra™ NeuraWrap™ Nerve Protector, Product Webpage, http://www.integra-ls.com/products/?product=198, Date unknown but believed to be prior to the filing date of the present application, 2 pages.

Kakisis, J., et al., Artificial blood vessel: The Holy Grail of peripheral vascular surgery, Journal of Vascular Surgery, vol. 41, Issue 2, 2003, pp. 349-354 (abstract only).

Biosingularity, Advances in biological systems, Google Ad, MIT Technology Review, 2006, 1 Page.

* cited by examiner

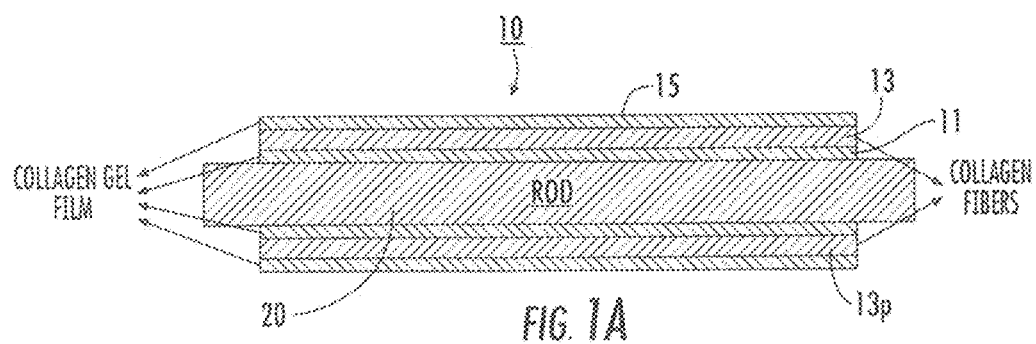
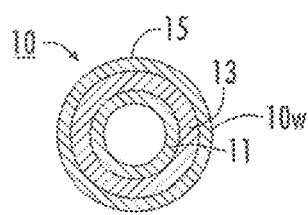

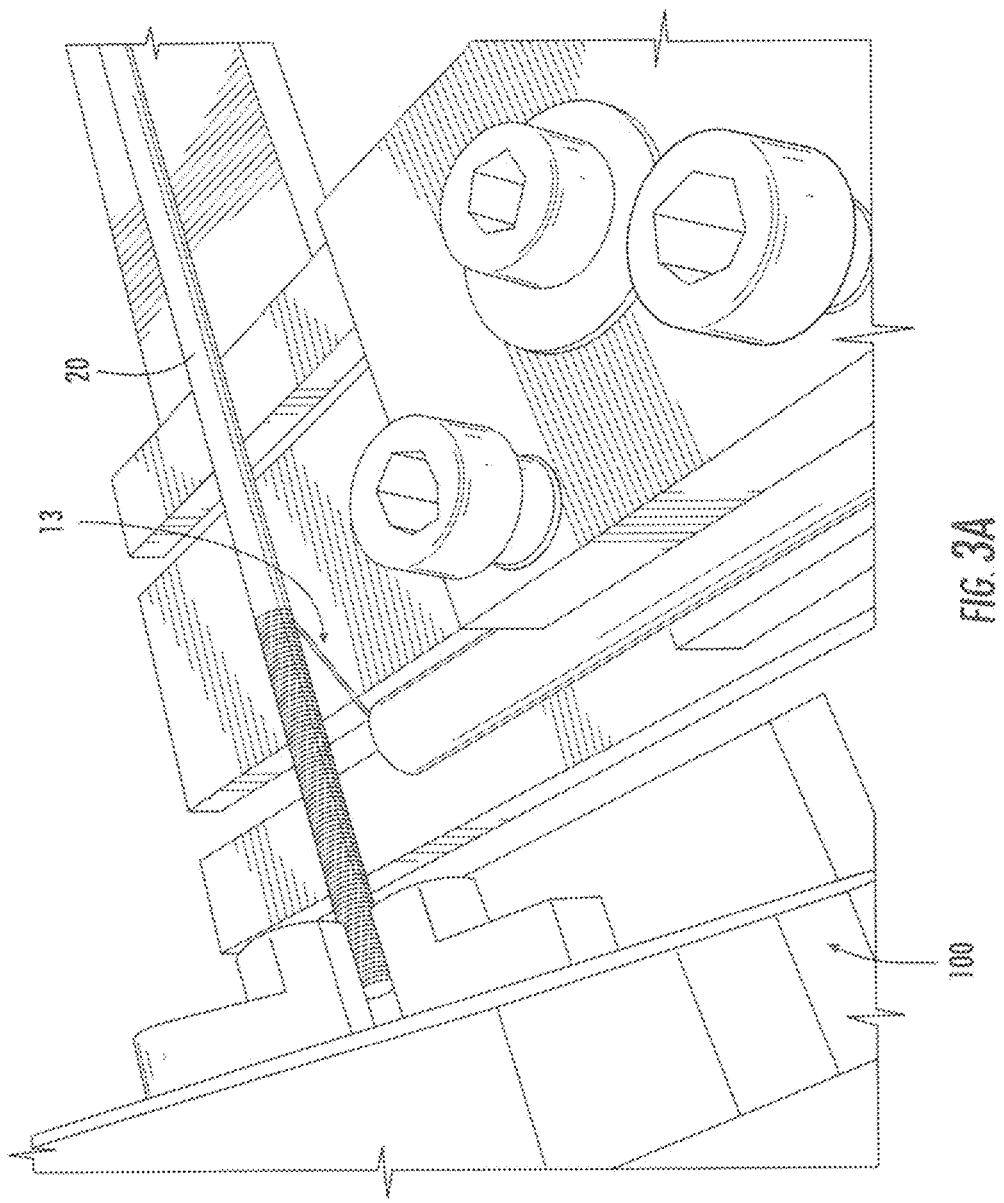

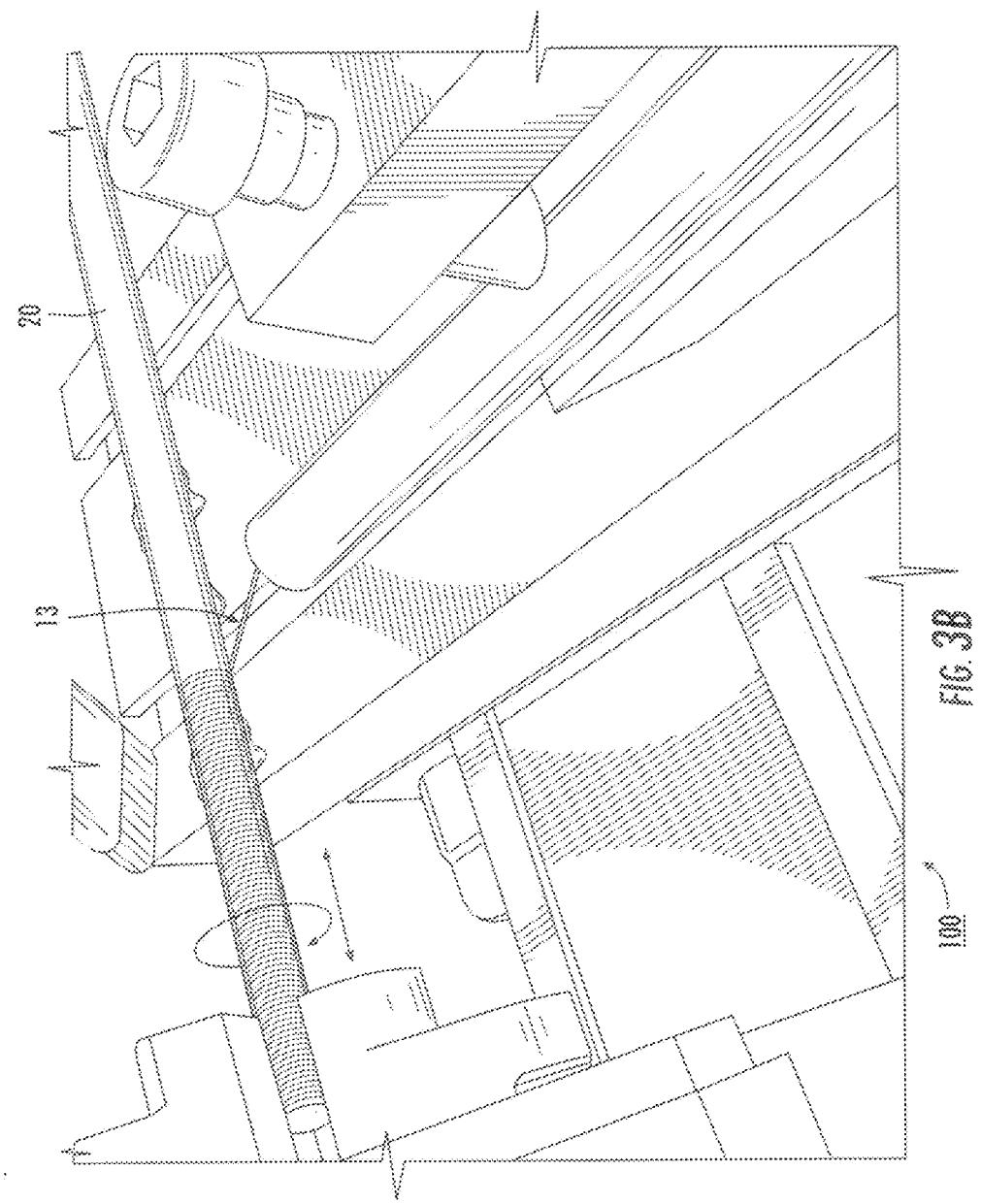

THE WINDING CAN BE CARRIED OUT SO THAT THE AT LEAST ONE FIBER TURNS ABOUT THE SUPPORT MEMBER IN ONE OF A CLOCKWISE OR COUNTERCLOCKWISE DIRECTION ALONG A FIRST LENGTHWISE DIRECTION FOR A FIRST LAYER, THEN REVERSES TO TRAVEL IN AN OPPOSING LENGTHWISE DIRECTION AND CONTINUES TO TURN ABOUT THE SUPPORT MEMBER IN THE SAME CLOCKWISE OR COUNTERCLOCKWISE DIRECTION TO FORM A SECOND OVERLYING ADJACENT LAYER.
180

FIG. 11

METHODS OF MAKING COLLAGEN FIBER MEDICAL CONSTRUCTS AND RELATED MEDICAL CONSTRUCTS, INCLUDING NERVE GUIDES AND PATCHES

RELATED APPLICATIONS

This application is a divisional of U.S. patent application Ser. No. 12/576,435, filed Oct. 9, 2009, which claims the benefit of and priority to U.S. Provisional Application Ser. No. 61/103,995 filed Oct. 9, 2008, and U.S. Provisional Application Ser. No. 61/138,165 filed Dec. 17, 2008, the contents of which are hereby incorporated by reference as if recited in full herein.

FIELD OF THE INVENTION

The invention relates to biomedical materials and products.

BACKGROUND OF THE INVENTION

Koob et al. have described methods of producing nordihydroguaiaretic acid (NDGA) polymerized collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, the contents of which are hereby incorporated by reference as if recited in full herein.

SUMMARY OF EMBODIMENTS OF THE INVENTION

Embodiments of the present invention are directed to methods of making collagen constructs for medical use and related constructs.

Particular embodiments are directed to nerve guides having a tube with a wall having at least three laminated layers, including an intermediate layer of at least one collagen fiber arranged in a repeating pattern sandwiched by a collagen film outer surface and a collagen film inner surface.

The collagen film can be applied as a collagen gel to and the tube can be cross-linked with nordihydroguaiaretic acid (NDGA) to create a polymerized collagen tube.

Some embodiments are directed to methods of manufacturing a medical construct. The methods can include winding at least one collagen fiber a number of revolutions about a length of a support member having a long axis, the winding can have at least one defined pitch and/or fiber angle relative to the long axis of the support member to form the construct.

The method may include placing a liquid or gel comprising soluble collagen onto the at least one wound collagen fiber during or after the winding step so that the elongate construct is wetted and/or so that the outer surface is covered in a collagen film, when the soluble collagen is dry.

The method may also optionally include providing a spooled supply of at least one collagen fiber for the winding step. The at least one collagen fiber may optionally be introduced to the support member from the spooled supply in a substantially dry state.

The winding step may be carried out to create multiple adjacent overlying layers of the at least one fiber, the adjacent layers being coextensive for at least a major portion of a length of the construct. The pitches on the different layers on some portion of each layer may differ. For example, the winding step can be carried out to have a first pitch for the winding of the at least one collagen fiber on the first layer and a second smaller or greater pitch for the winding of the at least one collagen fiber on the second layer.

In some particular embodiments, the at least one fiber on the second layer resides between gaps defined by the at least one fiber wound with the defined pitch on the first layer.

The method may include placing collagen gel about an outer surface of the support member before the winding step and allowing the collagen gel to dry to form a film on the support member. Then, the collagen fiber winding can be carried out while applying soluble collagen to a surface of the at least one fiber on the support member. The wound collagen fiber with the soluble collagen is actively or passively dried, then a collagen gel can be applied over the dried collagen fiber with the soluble collagen and, again allowed to dry, to form an outer layer of film.

Other embodiments are directed to medical devices. The devices may be a material, an implant themselves or on or in implants. For example, the devices can include a tube with a wall surrounding an axially extending cavity. The wall has at least one collagen fiber (typically of a continuous length of fiber) having a number of revolutions over at least a major length of the tube with a pattern of intersecting segments. The tube may also optionally have an inner layer of a collagen film and/or an outer layer of collagen film, each integrally attached to the at least one collagen fiber.

The at least one collagen fiber can be derived from soluble dermal collagen, and wherein the collagen film comprises soluble dermal collagen having a collagen concentration of between about 0.1-4% weight per volume.

Particular embodiments are directed to nerve guides. The nerve guides include a tube with a wall surrounding an axially extending cavity, the wall having at least one wound collagen fiber arranged with a number of revolutions over at least a major length of the tube on at least one layer. Optionally, the nerve guide can include an inner layer of a collagen film and/or an outer layer of collagen film which may be integrally attached to the collagen fiber.

The medical nerve guide or cuff can include an elastic tube with a wall surrounding an axially extending cavity. The wall can have at least one collagen fiber of a continuous length arranged in a fiber mesh pattern of intersecting segments over at least a major length of the tube. The at least one collagen fiber can be embedded in a collagen film that extends over interstitial spaces defined by the fiber mesh pattern.

Other embodiments are directed to medical patches. The patches have at least one collagen fiber having a length arranged in an angular pattern with adjacent layers defining fiber orientations that intersect. The patches may optionally have an inner layer of a collagen film and/or an outer layer of collagen film.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 1A is a schematic cross-section (in an axial direction) of an exemplary collagen fiber construct on an exemplary support member according to embodiments of the present invention.

FIG. 1B is an end view of the device shown in FIG. 1A (shown without the support member) according to embodiments of the present invention.

FIG. 3A is a top perspective view of a lathe that can be used to wind collagen fiber(s) onto a tubular support member according to embodiments of the present invention.

FIG. 3B is a side perspective view of the device shown in FIG. 3A.

FIG. 11 is a flow chart of an exemplary winding protocol according to particular embodiments of the present invention.

DETAILED DESCRIPTION

Figure 2B:
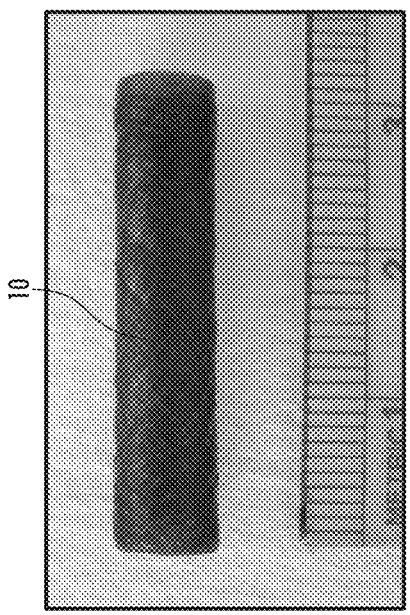
FIGS. 2A-2D are digital photographs of a prototype of a collagen fiber construct that may be particularly suitable for a nerve guide according to embodiments of the present invention.
Figure 2D:
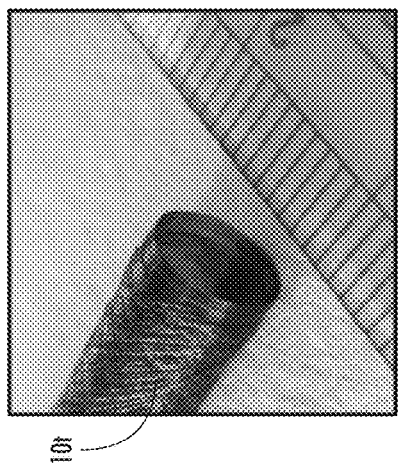
Figure 2A:
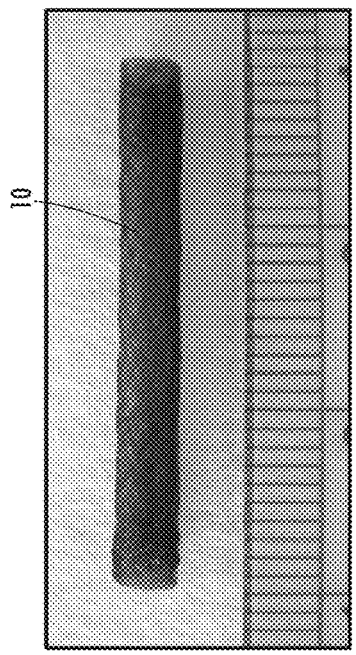
Figure 2C:
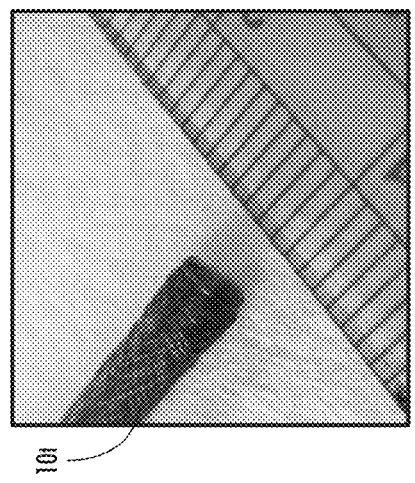

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The term "implantable" and derivatives thereof means the device can be inserted, embedded, grafted or otherwise acutely or chronically attached or placed in or on a patient. The term "construct" refers to a device and/or material in a final form for use or in a pre-final form. The term pitch" means winding or wound at an angle relative to a first plane normal to the longitudinal axis of a core or cavity.

The terms "winding" and "wound" and derivatives thereof means to wrap about an object or center at least once, typically repeatedly, e.g., to turn in a series of circular motions. In some embodiments, at least one collagen fiber (multiple fibers, one or more fiber bundles) turns or rotates its circumferential position about a centerline or long axis. The winding may define a coil (e.g., a series of connected typically substantially concentric rings or spirals), woven and/or braided fiber arrangement with a number of revolutions or turns about a core and/or tube, typically in a regular pattern (but an irregular pattern may also be used) about a length of at least one layer of a tube or cylindrical shape.

Embodiments of the present invention comprise collagen, typically dermal collagen. However, the collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized or soluble collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before, where used, oxidizing and polymerizing steps. The collagen can be in the form of microfibrils, fibrils, natural fibers, or synthetic fibers.

In some embodiments, the collagen can be solubilized, dissolved or otherwise transferred into an acid solution, for example, acetic acid (e.g., about 0.01M to about 1.0M, typically about 0.5M), hydrochloric acid (between about pH 1 to about pH 3, typically about pH 2.0), or any other suitable acid at appropriate concentration (e.g., about pH 1.0 to about pH 3.0, typically about pH 2.0). Dialysis may optionally be used to neutralize a soluble collagen solution. The collagen can also or alternatively be dissolved in a neutral buffered solution either with or without salts, e.g., phosphate buffer at about pH 7.0, or phosphate buffered saline at about pH 7.0. The phosphate buffer can be at any concentration of sodium phosphate between about 0.01 and 0.5, but more typically between about 0.02 and about 0.1M. The buffer can also be any buffer, including, but not limited to, for example, sodium acetate, HEPES, or MOPS. The collagen can be present in a quantity that is at least about 0.1% to about 10%, typically between 0.1% to about 5% (e.g., about 0.1, 0.2, 0.3, 0.4, 1.0, 2.0, 4.0%) by weight per volume, or by weight per volume in the neutral buffer solution before fibrillogenesis and fiber formation. In a dried fiber collagen, collagen can be present in an amount of weight by volume of between about 50-100% (e.g., at least about 75%, 90%, 95% or 100%) before crosslinking (where crosslinking is used).

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 μm in diameter. Natural fibers are above 50 μm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber.

Of course, synthetic collagen fibers can include non-collagenous components or biocompatible materials, such as particulates, hydroxyapatite and other mineral phases, or drugs that facilitate tissue growth or other desired effects. See, U.S. Pat. No. 6,821,530, incorporated herein by reference above. For example, the fibers and/or constructs formed from same, can include compositions that can contain carbon nano-tubes, zinc nano-wires, nano-crystalline diamond, or other nano-scale particulates; and larger crystalline and non-crystalline particulates such as calcium phosphate, calcium sulfate, apatite minerals. For example, the compositions can also or alternatively contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or fiber-derived constructs can contain cells, engineered cells, stem cells, and the like. Combinations of the above or other materials can be embedded, coated and/or otherwise directly or indirectly attached to the collagen fibers and/or construct formed of same.

The term "collagen gel" means a semi-solid (e.g., gelatinous density) material that includes collagen fiber, fibrils and/or microfibrils, typically dermal collagen, that has been acid or pepsin solubilized (e.g., soluble collagen) and processed to maintain the collagen in its molecular form. The collagen concentration of the soluble collagen and/or resulting soluble collagen gel can be between about 0.1% to about 4% weight per volume. The soluble collagen gel may be formed to be in a cylindrical shape of a defined length and diameter, typically with a diameter of between about 0.1 to 1 cm, and a length of between about 5 cm to about 100 m, more typically between about 1 m to about 50 m.

The collagen fibers and collagen gel can be produced in batch or continuous-type systems, including wet gel collagen extrusion systems, which produce cylindrical lengths of gel that can be allowed to substantially dry (actively or passively) to obtain a suitable length of fiber. Examples of some collagen fiber production processes that can generate soluble collagen in suitable lengths are described in U.S. Pat. No. 6,565,960, and pending U.S. Patent Application Publication No. US-2008-0188933-A1, the contents of which are hereby incorporated by reference.

The collagen fibers can be spooled for supplying to an automated or semi-automated winder to form the biomedical construct. The collagen fibers may be formed with a relatively thin diameter, such as, for example between about 0.05 mm to about 0.2 mm (average), such as about 0.08 mm dry diameter (average) and about a 0.13 mm wet diameter (average).

The term "film" refers to a thin layer of collagen gel that has dried. The film is typically present in a thickness that is between about 5 and 200 microns. The film may be permeable and flexible and optically transmissive, e.g., translucent or transparent, or may be opaque. Several layers of the gel can be applied to generate the desired film thickness or coverage. The color or transmissive characteristics may change when hydrated. The film can infuse into, migrate and/or bond to a coiled or wound (dry) collagen fiber to form a collagen fiber laminate. The gel/film is not required, but where used can provide a smooth (and typically a substantially constant diameter) surface over or under the fiber.

Referring now to the figures, FIG. 1A, an exemplary elongate construct 10 is shown on a support member 20. As shown, the construct 10 includes an inner layer of collagen film 11, an intermediate layer of at least one wound collagen fiber 13, and an outer layer of collagen film 15.

In other embodiments, the construct 10 can be formed without the inner and/or outer layer of film 11 and/or may optionally include other materials or constituents and/or layers. For example, hydroxyapatite can be placed into the collagen fiber and/or collagen gel material. This configuration can be particularly suitable to augment interference screw fixation of autograft tendons.

As shown in FIG. 1B, the construct 10 can have a wall 10w with a suitable thickness defined by the at least one collagen fiber 13 and the film layers (where used) and/or other coatings and/or materials placed thereon. The construct 10 can have an open through cavity or may be filled or partially filled with a nerve-growth media or other therapeutic material (e.g., an anti-inflammatory, antibiotic and/or the like).

Figure 3C:
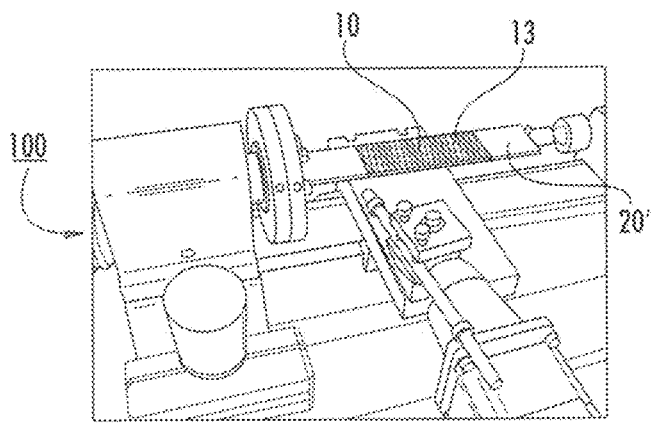
FIG. 3C is a side perspective view of the lathe with a substantially planar elongate support member according to embodiments of the present invention.
Figure 3D:
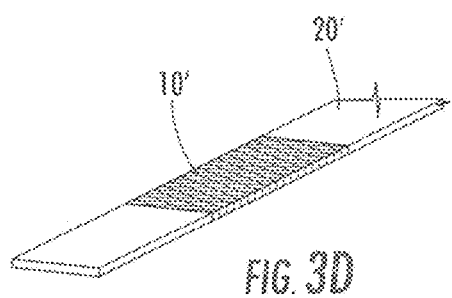
FIG. 3D is a side perspective view of a planar support member with a wound collagen fiber(s) according to other embodiments of the present invention.
Figure 3E:
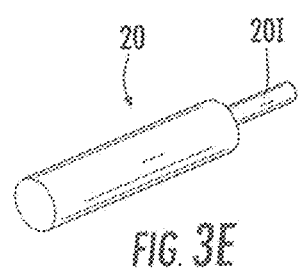
FIG. 3E is a side perspective view of a tubular support member with an insert according to embodiments of the present invention.

As also shown, the at least one collagen fiber 13 has an angular fiber pattern 13p of repeating intersecting collagen fiber segments along its length. The angular pattern 13p can be defined by a number of revolutions of the at least one fiber 13 about the support member 20 at a given pitch or pitches for at least one layer (typically more than one layer). The support member 20 is used to wrap the at least one collagen fiber around its exterior surface to form a desired shape. The support member 20 can include a lubricious and/or smooth surface, or an embossed surface with lower contact surface area, typically of a polymer material. In other embodiments, the support member 20 can include an anti-slip surface with ridges or a sleeve can be placed over the support member (not shown) to contact the next layer (e.g., inner film 11 or fiber 13). In some embodiments, the support member 20 comprises Teflon® or other suitable low friction and/or anti-stick material. The support member 20 can be tubular, e.g., cylindrical, as shown in FIGS. 1A, 3A, 3B and 3E or may be substantially flat and rectangular 20' as shown in FIGS. 3C and 3D. Other geometries may also be used, such as, for example, a frustoconical or funnel shape. Typically, the support member 20 is elongate and has a substantially circular, oval, polygonal or other cross-sectional shape.

Figure 4:
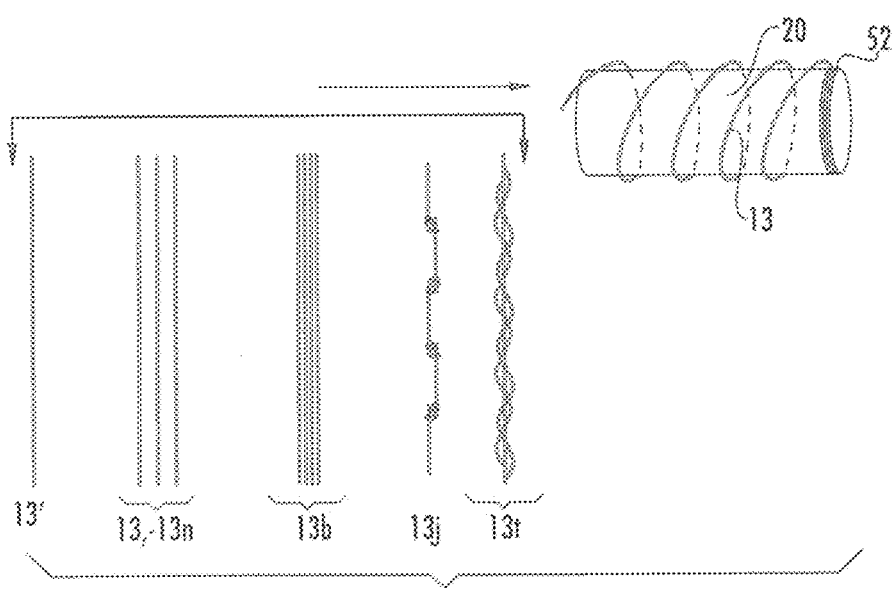
FIG. 4 is a schematic illustration of different collagen fiber configurations that may be used for winding a construct according to embodiments of the present invention.

The at least one collagen fiber 13 can be organized into various arrays including braids, weaves, knits, parallel arrays, and various patterns. The orientation of one or more of the fibers 13 within the resulting material 10 (see, e.g., FIGS. 2A-2D) can be targeted to meet the specific mechanical requirements of the medical application. Fiber density can vary from dense to loose geometries and the numbers and size of the one or more collagen fibers used can vary as well as the thickness of the film to provide specific mechanical properties. The fiber(s) 13 can be continuous length fibers or may be formed by attaching a series of collagen fibers in an end-to-end orientation 13j (FIG. 4).

Figures 8A, 8B:
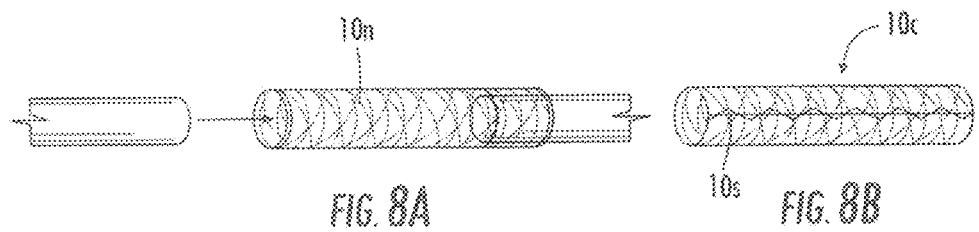
FIG. 8A is a schematic illustration of a collagen nerve guide according to embodiments of the present invention.
FIG. 8B is a schematic illustration of a collagen cuff according to embodiments of the present invention.

FIGS. 2A-2D are digital photographs of a prototype of a construct 10. This construct 10 may be particularly suitable as a nerve tube or guide 10n (FIG. 8A). The construct 10 is tubular 10t with an open cavity and has a flexible elastic configuration. The construct 10 may be configured as a nerve guide 10n. The nerve guide 10n can be formed using a single fiber 13 formed in wound multiple layers, the fiber 13 can have a length between about 1-6 m, typically about 5 m. The nerve guide 10n can be formed using a single fiber 13 of a continuous length that is wrapped in several layers about the support member 20. Use of a single fiber 13 can reduce the likelihood of any fraying associated with multiple fibers (such as those wound in one lengthwise direction). The nerve guide 10n can have a length between about 1 cm to about 6 cm (or more), and the inner diameter can be between about 1-10 m with the wall thickness being about 0.1 mm to about 3 mm.

The construct 10 can have reversible elasticity with sufficient rigidity or strength to prevent undue nerve compression, while allowing flexibility sufficient to allow the construct 10 to spring back into its original shape after being exposed to a strain or tension caused by normal body movement that deforms the shape. The nerve guide 10n can be used for any nerve location, e.g., peripheral nerves (such as in a hand or finger), spinal cord nerves, and the like. The construct 10 can be used for other repairs or treatments as will be discussed further below. The construct 10 is biocompatible (or at least non-cytotoxic) and can provide a desired half-life suitable for its intended function.

The construct 10 and/or the fiber 13 can be cross-linked with a suitable polymerizing material, such as, but not limited to, NDGA, or may be used in a non-cross-linked state. The NDGA cross-linking can increase the strength of the device 10 but may decrease the resiliency, elasticity or flexibility. In some embodiments, the collagen fiber 13 is not cross-linked during the winding process, but may optionally be cross-linked after the winding process (typically after the collagen film has been applied to the outer surface and dried).

The support member 20 can be configured to facilitate removal of the construct 10. For example, the construct 10 may be wound tightly against the outer surface of the support member 20 and allowed to dry. The support member 20 can be configured to reduce in cross-sectional size or disassemble with the construct 10 held thereon to allow easy removal of the elongate construct. In some embodiments, the support member 20 can be a multi-piece device that provides this size change. In other embodiments, the support member 20 may be cooled while the construct is heated to provide a size difference. In particular embodiments, the support member 20 can cooperate with an insert 201 (FIG. 3D) that provides the desired size adjustability. In other embodiments, the construct 10 can be removed from the support member without such a size adjustment (e.g., its inner surface may be sufficiently lubricous or a suitable liquid or other material can be used to slide the construct off the support member. In other embodiments, the construct 10 can be cut in a lengthwise (e.g., "X") direction and taken off the support member 20. In some embodiments, the construct 10 may be cut or otherwise separated in a long axis direction with a longitudinal slit 10s and used for a cuff 10c (FIG. 8B) that can be positioned about a nerve or other tissue to protect that tissue (and the cuff may be sutured together along at least a portion of the long axis and/or may be sutured or otherwise anchored into position). The cuff 10c may be configured to provide a snug or alternatively, a non-constricting, encasement for injured peripheral nerves for protection of the neural environment. The wall of the cuff with the longitudinal slit 10s can be spread open for easy placement over the injured nerve or other target tissue. The resilience of the collagen conduit allows the cuff to recover and maintain closure once the device is placed around the nerve.

As shown in FIGS. 3A-3B, the construct 10 can be made by winding at least one collagen fiber 13 around a support member 20 using a computer-guided and/or controlled lathe system 100. The lathe system can be configured to rotate the support member 20 and to move the support member back and forth in a length direction to alter the location of the fiber on the support member 20 relative to the introduction point of the fiber (e.g., the fiber introduction point may be stationary). In other embodiments, the fiber(s) 13 can be supplied through a head that moves relative to the support member 20 (e.g., the support member can be stationary) or both the fiber introduction head and the support member may move relative to teach other.

Different size (e.g., diameter) support members 20 can be used depending on the target product. For example, transverse small cross-section support members (e.g., diameter rods) can be used for manufacturing devices for use in vein and artery replacements or repairs, while larger transverse cross-section support members (e.g. diameter rods) can be used to manufacture devices for aortic or large artery replacements or repairs and/or various shunts.

An example of a small lathe 100, typically a micro or miniature lathe, suitable for fabricating embodiments of the constructs is the Model 4410 lathe available from Sherline Products, Inc., having a place of business in Vista, Calif. Two user-selectable inputs can operate the lathe system: one controls the speed that the support member that spins and the other controls the pattern (fiber angle) in which the at least one fiber 13 is laid onto the support member. The operation can be configured so that the fiber is self-pulling from a spool in communication with a channel in the feeder head based on the speed of the spinning support member 20. The lathe 100 can co-wind a plurality of fibers or fiber bundles substantially concurrently about the support member 20.

The at least one collagen fiber 13 can be coated with one or more layers of collagen gel 11, 15 and/or other suitable bio-compatible material during and/or after winding the at least one collagen fiber 13 to seal the fiber(s) 13 within the biocomposite material and/or to form a smooth inner and/or outer surface of the construct 10. FIG. 3B illustrates that collagen gel can be applied to the fiber 13 on the support member during the winding. FIG. 3B illustrates that a brush 111 can be used to apply the gel. Other application techniques may be used, such as spray, pour, drop, and the like. The application of the soluble collage gel may be manual or automated and applied by electro-mechanical devices.

The winding can be performed so that at least one layer of the at least one collagen fiber has a substantially constant pitch for at least a major portion of a length thereof or so that at least one layer of the at least one collagen fiber has a variable pitch for at least a major portion of a length thereof.

FIG. 4 illustrates that different configurations of fibers 13 may be used. Examples of fiber configurations include a single fiber $13_1$, a plurality of fibers $13_1$-$13n$ (typically n=2 to 100) that can be concurrently co-wound about the support member 20, a fiber bundle 13b, and a twisted, woven or braided fiber bundle 13t. For the fiber bundles 13b, 13t, two or more fibers 13 can be grouped together to form the fiber bundle 13b, 13t and that bundle 13b, 13t applied or wrapped about the support member 20, similar to a single fiber. One or more fiber bundles 13b, 13t may be used to form the construct 10. Combinations of the different fiber types may also be used for some constructs 10. That is, for example, a twisted fiber 13t can be co-wound with a single fiber $13_1$ and/or a single fiber $13_1$ may be used to form one layer and a twisted 13t to form a different layer, and the like.

The collagen fiber 13 can be wound using various fiber angles (e.g., pitch angles), such as, angles between about 2-70 degrees, typically between about 5-60 degrees, such as, for example, 5, 10, 15, 20, 25, 30, 35, 40, 45, 50, 54 and 55 degrees, or other odd or even numbers between 5-70. Where constructs of multiple layers are used, one layer may have a first pitch and another layer may have a different pitch.

Figure 5A:
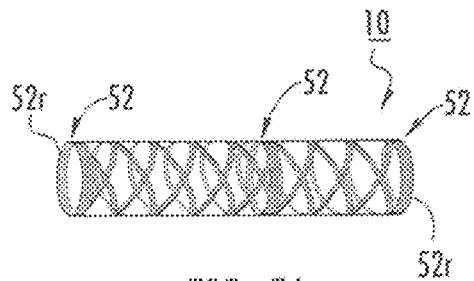
FIG. 5A is a schematic illustration of a tubular construct with segments having increased fiber density according to embodiments of the present invention.
Figure 5B:
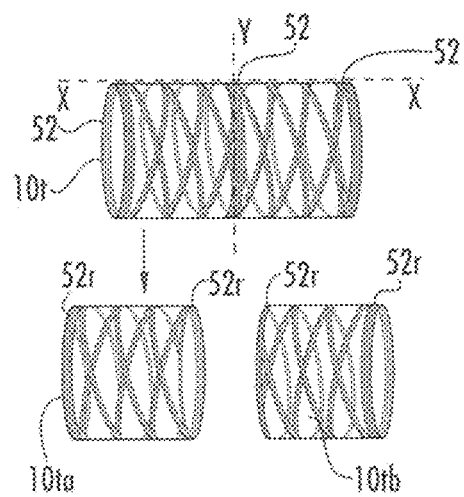
FIG. 5B is a schematic illustration showing that the tubular structure of FIG. 5A can be separated or cut into multiple different components (shown as two) according to embodiments of the present invention.

FIG. 5A illustrates that a construct 10 can be wound with increased fiber density 52 along certain segments, typically forming end rings 52r. This increased fiber density 52 can provide sufficient rigidity to allow a suture to attach thereto. As shown in FIG. 5A, the construct 10 is tubular 10t and may optionally include an increased density segment 52 at an intermediate location. FIG. 5B illustrates that the construct 10 can be used as formed, or may be cut or separated along a Y-axis into two components 10ta, 10tb. For the latter, the intermediate increased density ring 52 can form end rings for the separated construct 10ta, 10tb.

Figure 6A:
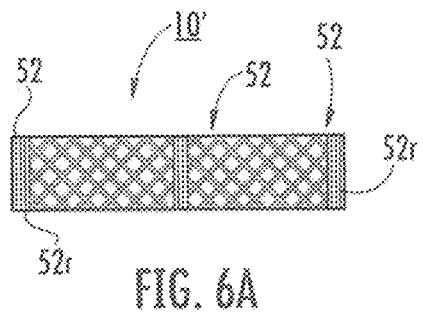
FIG. 6A is a schematic illustration of a substantially planar construct with segments having increased fiber density according to embodiments of the present invention.
Figure 6B:
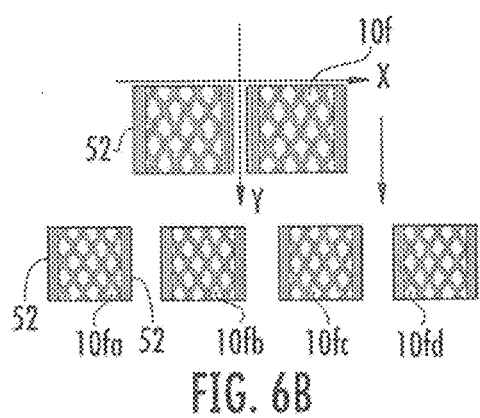
FIG. 6B is a schematic illustration of the construct shown in FIG. 6A illustrating that the construct can be separated into multiple components (shown as four) according to embodiments of the present invention.

FIG. 6A illustrates a construct 10 that is relatively flat 10f and/or rectangular. Again, the construct 10f can optionally include increased fiber density segments 52 that may be suitable for end rings 52r. FIG. 6B illustrates that the construct 10f can be cut along the X-axis and separated into at least two components that form biocompatible patches. The intermediate increased density ring(s) 52, where used, can optionally form end rings 52 for the separated construct 10fa, 10fb, etc.

Figure 7:
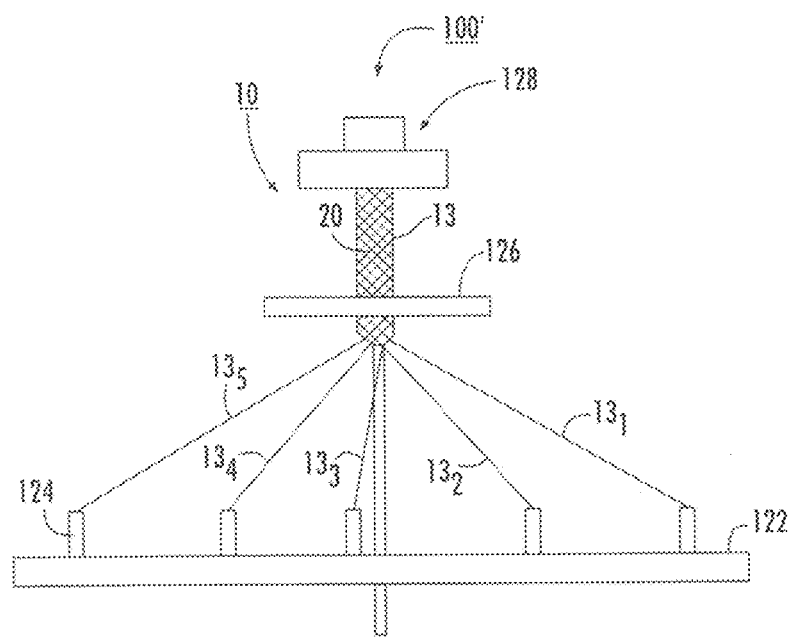
FIG. 7 is a front view of a winding apparatus that can be used to wind (braid) collagen fiber according to embodiments of the present invention.

FIG. 7 illustrates an example of another automated winding system 100' that can be used to form the construct 10. This embodiment uses several fibers 13, each independently wound and/or wrapped to weave or braid the fibers about the support member 20 to form the construct 10. The system 100' includes a plate 122 supporting spindles 124, a forming plate 126, a support member (shown as a cylindrical mandrel) 20 that extends through an aperture in the forming plate 126, and braid puller 128. An exemplary microbraider is believed to be available from Kokubun Ltd of Japan. See also, FIG. 2 and col. 2 of U.S. Pat. No. 7,135,040, the content of which is hereby incorporated by reference.

The fibers 13 can be wound before or after cross-linking (or not cross-linked at all). If wound before, the fibers can, where desired, be polymerized with any suitable cross-linking materials, to promote collagen organization, such as, for example, NDGA, but other cross-linking materials may be used, including, for example, glutaraldehyde. The (dried) collagen fiber can also be treated with other methods to improve the tensile properties of the fiber. The (dried) collagen fibers 13 can be cross-linked with agents such as glutaraldehyde, formaldehyde, epoxy resins, tannic acid, or any other chemical agent that produces covalent cross-links between collagen molecules within fibrils or between fibrils. Alternatively, the fiber 13 can be treated to induce cross-linking between collagen molecules such as, but not limited to, one or more of a carbodiimide treatment, ultraviolet irradiation either with or without carbohydrates to initiate glycation adducts, and dehydrothermal treatment coupled with any of the aforementioned methods.

Figure 9:
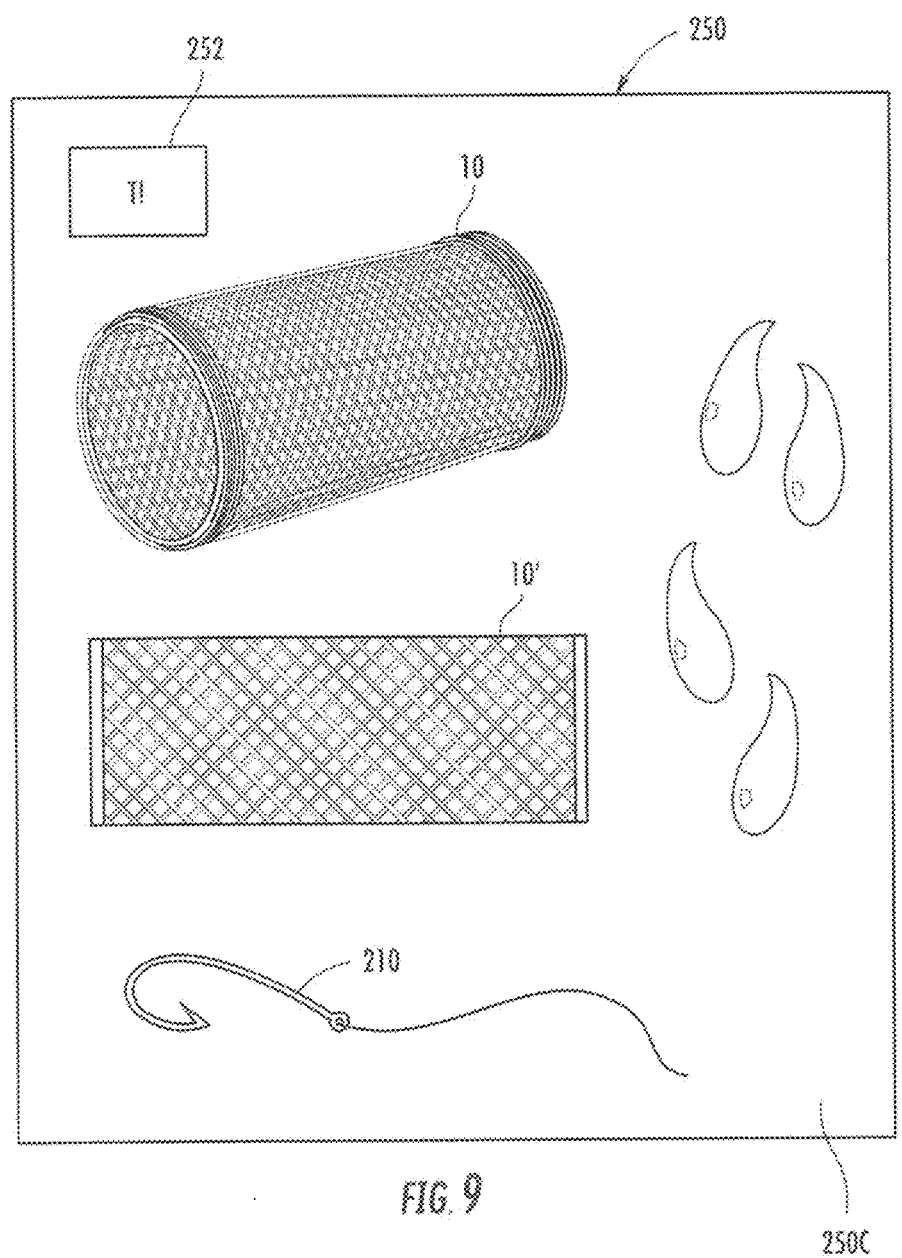
FIG. 9 is a schematic illustration of a medical kit according to embodiments of the present invention.

FIG. 9 illustrates a medical kit 250 that includes a medical device or implant 10 or 10'. The kit 250 may optionally include other components, such as, for example, a container of surgical adhesive, sutures 210, suture anchors, and the like. The device or implant 10, 10' may be held hydrated in a flexible sealed package of sterile liquid 230. The kit 250 may include a temperature warning so that the construct 10, 10' is not exposed to unduly hot temperatures that may degrade the implant. A temperature sensor 252 may optionally be included on the package of the kit to alert the clinician as to any excessive or undue temperature exposure prior to implantation. For example, it may be desirable to hold or store the kit 250 (and implant or device 10, 10') at a temperature that is less than about 37° C. and/or 100° F. prior to implantation. The kit 250 may be packaged in a housing with a temperature controlled or insulated chamber 250c to facilitate an appropriate temperature range.

Figure 10:
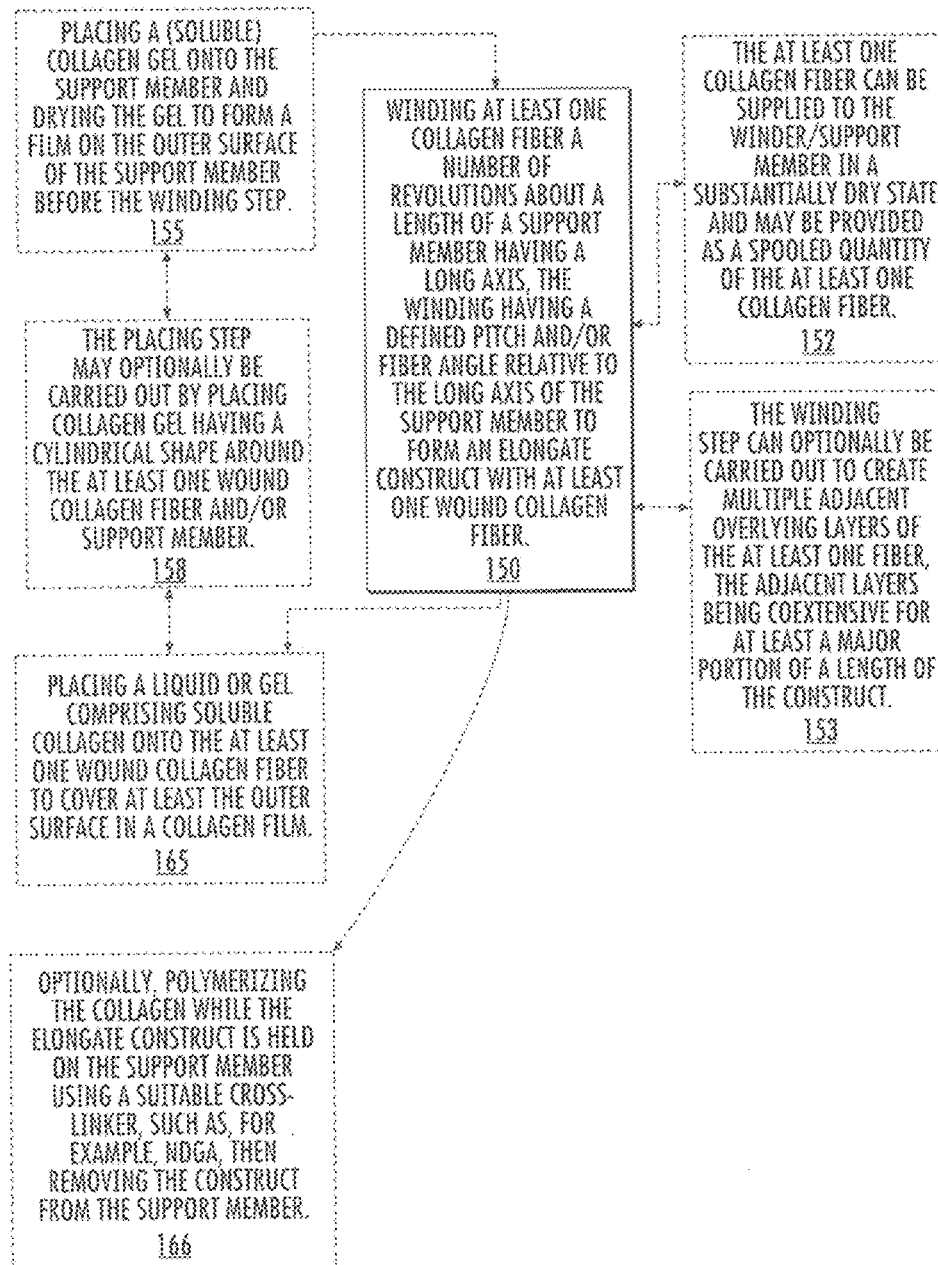
FIG. 10 is a flow chart of operations that can be used to fabricate a construct according to embodiments of the present invention.

FIG. 10 is a flow chart of operations that can be used to carry out embodiments of the present invention. In some embodiments, the at least one collagen fiber is wound a number of revolutions about a length of a support member having a long axis. The winding can have a defined pitch and/or fiber angle relative to the long axis of the support member to form an elongate construct with at least one wound collagen fiber (block 150). The winding step can form multiple overlying layers of the at least one collagen fiber in one or more fiber angles so that the at least one fiber intersects itself at different locations along a length of the construct.

Optionally, a collagen gel can be placed onto the support member and the gel can dry to form a film on the outer surface of the support member before the winding step (block 155). The collagen film can be dried or allowed to dry on the support member (e.g., rod). As the fiber(s) is wound about the support member, a soluble collagen can be applied (e.g., wrapped, painted, sprayed, dripped and the like) onto the fiber(s) and/or support member so that the fiber(s) become wet while one or more layers are wound on the lathe.

The at least one collagen fiber can be supplied to the winder/support member in a substantially dry state and may be provided as a spooled (dry) quantity of the at least one collagen fiber (block 152). The fiber(s) can be supplied and wound in a non-cross-linked state.

In some embodiments, the winding step can be carried out to create multiple adjacent overlying layers of the at least one fiber, the adjacent layers being coextensive for at least a major portion of a length of the construct (block 153). A liquid or gel comprising soluble collagen can be placed onto the at least one wound collagen fiber to cover at least the outer surface in a collagen film (block 165).

Optionally, the placing of the collagen gel or liquid is carried out by placing collagen gel having a cylindrical shape around the at least one wound collagen fiber and the support member (block 158).

Optionally, the collagen can be polymerized while the elongate construct is held on the support member using a suitable cross-linker, such as, for example, NDGA, then removing the construct from the support member (block 166).

The winding can be carried out so that the at least one fiber turns about the support member in one of a clockwise or counterclockwise direction along a first lengthwise direction for a first layer, then reverses to travel in an opposing lengthwise direction and continues to turn about the support member in the same clockwise or counterclockwise direction for a second adjacent layer (block 180, FIG. 11). Alternatively, in particular embodiments, the winding may be carried out so that the at least one collagen fiber turns (is wrapped) about the support member in one of a clockwise or counterclockwise direction along a first lengthwise direction for a first layer, then reverses to travel in an opposing lengthwise direction and turns about the support member in the other clockwise or counterclockwise direction a second adjacent layer.

In some embodiments, the winding step has a first pitch for the winding of the at least one collagen fiber on the first layer and a second smaller or greater pitch for the winding of the at least one collagen fiber on the second layer. In some embodiments, the at least one fiber on the second layer resides between gaps defined by the at least one fiber wound with the defined pitch on the first layer.

The method can include cutting the construct in an axial direction to form a flat collagen fiber patch. The method can include winding the collagen fibers in a plurality of axially spaced apart segments with increased collagen fiber density, at least some of which are provided as reinforced segments for suturing. The reinforced segments can be formed at end portions of the tube and optionally at one or more intermediate locations therebetween. The methods can produce a nerve guide having sufficient strength and elasticity to withstand buckling and to be able to bend and to elastically return to its original shape after bending to inhibit occlusive pressures or restrictions on nerves.

Embodiments of the invention can be used for a number of different medical applications, including, but not limited to, nerve guides, wound bed patches, muscle or organ patches, cardiac patches, valve replacements or repairs, hernia patches, skin patches, burn treatment patches, skin/tissue repair patches or cuffs, blood vessel (artery, vein, and the like) repairs, sleeves that can reside about repairing tendon to prevent or inhibit adhesions, indwelling tubes for delivery of therapeutic agents, ducts such as lymphatic, hepatic, pancreatic and cystic ducts, tubes such as ureter and urethra tubes and the like.

The present invention is explained in greater detail in the following non-limiting Examples.

EXAMPLE

FIGS. 2A-2D illustrate exemplary sleeves or tubes of wound NDGA-collagen fibers that may be particularly suitable for nerve guides. The inner diameter of the tube can vary between about 1 and 10 mm. The thickness of the wall can vary between about 0.1 and 3 mm. The length of the tube can vary from between about 1 to 6 cm or more.

The tube can be made of dermal collagen that is acid or pepsin soluble. The soluble collagen can be made by neutralizing acid soluble collagen and keeping the soluble collagen at a desired low temperature to maintain the collagen in molecular form, (e.g., about 4° C.). Collagen gels can be produced from acid soluble collagen by neutralization, injection molding in a Teflon® tube of diameter between 0.1 cm to 1.0 cm and incubation for at least about 4 hours at 37° C. The resulting gel can be extruded into deionized water to form a gel cylinder with a diameter between about 0.1 cm to 1.0 cm (and can have a length between about 1-100 m. Collagen concentration of the soluble collagen and collagen gel can be from about 0.1-4% weight per volume. The gel cylinder can be used in the gel form or allowed to dry, actively or passively (suspended in air), to form a collagen fiber having a diameter between about 0.05 mm (average) to about 0.2 mm (average).

The first step to make this prototype tube is to wrap the collagen gel of specified collagen concentration and diameter onto a Teflon® rod of selected diameter. The collagen gel layer was allowed to dry on the rod at room temperature to form a thin layer of collagen film. The thickness of this collagen film can be varied by applying more or less layers of collagen gel, either is a single application of in several applications.

The second step is to wind dry collagen fibers on to the collagen film coated Teflon® rod. The pitch of the fiber relative to the long axis of the tube can be specified. The thickness of the collagen winding can be adjusted, for example, corresponding to the number of layers of fibers that are laid on (and/or the number of fibers bundled together for the winding). During the fiber winding process, soluble collagen is applied (e.g., painted) onto the surface of the laid-on fibers. The thickness of the final soluble collagen layer can be varied to achieve specific thickness. The soluble collagen coated fiber wound cylinder is allowed to dry.

The third step in making the tube is the same as the first step, e.g., to wrap a collagen gel on to the collagen fiber would Teflon® rod and the gel layer is allowed to dry to form a collagen film enwrapping the collagen fiber tube. The thickness of the penultimate collagen film can be varied by the number of layers of wrapped gel.

The dried tube can be used "as-is" (used in a non-crosslinked state and hydrated when in the body or prior to placement in the body), or it can be cross-linked with any agent or action that cross-links the collagen. The (nerve) tube is then taken off the Teflon® rod. In the present example, the tube is cross-linked with nordihydroguaiaretic acid (NDGA), see, e.g., U.S. Pat. No. 6,565,960, and U.S. Patent Application Publication No. US-2008-0161917-A1, the contents of which are hereby incorporated by reference as if recited in full herein.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of manufacturing a medical construct, comprising:
   winding at least one collagen fiber a number of revolutions about a length of a support member having a long axis, the winding having at least one defined pitch and/or fiber angle relative to the long axis of the support member to form the construct, wherein the winding comprises winding a continuous length of the at least one collagen fiber at a first pitch on a first layer and continuing winding of the at least one collagen fiber at a second smaller or greater pitch on a second layer over the first layer; and
   placing a gel comprising soluble collagen onto the at least one collagen fiber during, after or during and after the winding step so that an outer surface thereof comprises a collagen film when the soluble collagen is dry, wherein the collagen film comprises collagen fibers, fibrils and/or microfibrils.

2. A method according to claim 1, wherein the first and second layers of the at least one collagen fiber define a pattern of intersecting segments with interstitial spaces therebetween, and wherein the collagen film extends across the interstitial spaces.

3. A method of manufacturing a medical construct, comprising:
   winding at least one collagen fiber a number of revolutions about a length of a support member having a long axis and successively in first and second opposing directions to form overlapping layers of the at least one collagen fiber, the winding having at least one defined pitch and/or fiber angle relative to the long axis of the support member along the first direction corresponding to a first layer and a different at least one defined pitch and/or fiber angle relative to the long axis of the support member along the second opposing direction corresponding to a second layer to form the construct, wherein the winding in the first and second opposing directions forms a series of a plurality of intersecting circumferentially spaced apart segments of the overlying layers of the at least one collagen fiber; and
   providing a spooled supply of a continuous length of the at least one collagen fiber that is between about 1 m to about 100 m for the winding step.

4. A method according to claim 3, wherein the at least one collagen fiber is introduced to the support member from the spooled supply in a substantially dry state, and wherein each intersecting segment of a respective series are adjacent to a common longitudinal position of the construct.

5. A method according to claim 1, wherein the winding step is carried out to create greater than two adjacent overlying layers of the at least one collagen fiber, the adjacent layers being coextensive for at least a major portion of a length of the construct, wherein the overlying layers form a series of a plurality of intersecting circumferentially spaced apart segments of the at least one collagen fiber, and wherein each intersecting segment of a respective series are adjacent a common longitudinal position of the construct.

6. A method according to claim 1, wherein the at least one collagen fiber comprises at least one collagen fiber that has a length that is formed by connecting a series of collagen fibers in an end-to-end orientation.

7. A method according to claim 5, wherein the winding is carried out so that the at least one collagen fiber turns about the support member in one of a clockwise or counterclockwise direction along a first lengthwise direction for the first layer, then reverses direction and turns about the support member in the other clockwise or counterclockwise direction in an opposing lengthwise direction for the second layer, then repeats the first direction for a third layer and repeats the second direction for a fourth layer.

8. A method according to claim 1, wherein the at least one collagen fiber on the second layer resides between gaps defined by the at least one collagen fiber wound with the first pitch on the first layer.

9. A method according to claim 1, further comprising placing a gel of soluble collagen having a substantially cylindrical shape on the support member before the winding step.

10. A method according to claim 1, wherein the support member is substantially cylindrical.

11. A method according to claim 1, wherein the support member is substantially rectangular.

12. A method of manufacturing a medical construct, comprising:
placing a collagen gel about an outer surface of a support member; and
allowing the collagen gel to dry to form a film on the support member; then
winding the at least one collagen fiber about the support member over the film while applying a liquid and/or gel of soluble collagen to a surface of the at least one collagen fiber on the support member, wherein the winding the least one collagen fiber comprises winding the at least one collagen fiber a number of revolutions about a length of the support member having a long axis, the winding having at least one defined pitch and/or fiber angle relative to the long axis of the support member to form the construct, wherein the winding comprises winding a continuous length of the at least one collagen fiber at a first pitch on a first layer and winding the at least one collagen fiber at a second smaller or greater pitch on a second layer over the first layer; then
allowing the wound collagen fiber with the soluble collagen to dry; and then
applying a collagen gel over the dried collagen fiber with the soluble collagen and allowing the applied collagen gel to dry to form an outer layer of film.

13. A method according to claim 1, further comprising, after the placing of the gel comprising the soluble collagen on the at least one collagen fiber, allowing the at least one collagen fiber comprising the soluble collagen to dry, then polymerizing the at least one collagen fiber while the construct is held on the support member, then separating the polymerized at least one collagen fiber from the support member.

14. A method according to claim 1, wherein the winding step is carried out using a lathe to automatically wind the at least one collagen fiber about the support member at a desired fiber angle and at a desired rotating speed.

15. A method according to claim 1, further comprising cutting the construct in an axial direction to form a substantially flat collagen fiber patch.

16. A method of manufacturing a medical construct, comprising:
winding at least one collagen fiber a number of revolutions about a length of a support member having a long axis, the winding having at least one defined pitch and/or fiber angle relative to the long axis of the support member to form the construct, wherein the winding comprises winding a continuous length of the at least one collagen fiber at a first pitch on a first layer and continuing winding the at least one collagen fiber at a second smaller or greater pitch on a second layer over the first layer, and wherein the winding further comprises winding the at least one collagen fiber in a plurality of axially spaced apart segments with increased collagen fiber density, at least some of which are provided as reinforced segments for suturing.

17. A method according to claim 16, wherein the reinforced segments are formed at end portions of the construct.

18. A method according to claim 16, wherein the reinforced segments are formed at end portions of the construct and at least one intermediate location therebetween.

19. A method of manufacturing a medical construct, comprising:
winding at least one collagen fiber a number of revolutions about a length of a support member having a long axis in a plurality of overlying layers, the winding having at least one defined pitch and/or fiber angle relative to the long axis of the support member to form the construct with the overlying layers providing a series of a plurality of intersecting circumferentially spaced apart segments of the at least one collagen fiber, wherein each intersecting segment of a respective series resides adjacent a respective longitudinal position of the construct,
wherein the construct is a nerve cuff, and wherein the at least one collagen fiber is a single collagen fiber that is wound in a first axial direction relative to the support member for a length of the construct then wound in a second opposing axial direction relative to the support member for a length of the construct to provide the overlying layers thereby providing an anti-fray configuration for the nerve cuff.

20. A method of manufacturing a medical construct, comprising:
winding at least one collagen fiber a number of revolutions about a length of a support member having a long axis, the winding having at least one defined pitch and/or fiber angle relative to the long axis of the support member to form the construct,
wherein the construct is a tube and the at least one collagen fiber is a single fiber that is wound in a first axial direction for a length of the tube, then wound in a second opposing axial direction for a length of the tube to form multiple overlying layers of the single collagen fiber forming a fiber mesh pattern with interstitial spaces, and wherein a collagen film resides on at least one of the inner and outer surfaces of the construct and defines a smooth surface.

21. A method according to claim 1, wherein the at least one collagen fiber includes at least one collagen fiber bundle.

22. A method according to claim 12, wherein the at least one collagen fiber is a single fiber.

23. A method according to claim 1, wherein the winding step is carried out to form multiple overlying layers of the at least one collagen fiber so that the at least one collagen fiber intersects itself at a plurality of different locations along a length of adjacent layers of the construct.

24. A method according to claim 1, wherein the at least one collagen fiber is a plurality of collagen fibers, and wherein the winding step comprises winding the plurality of collagen fibers substantially concurrently about the support member.

25. A method according to claim 12, wherein the at least one collagen fiber is a plurality of multiple-fiber synthetic collagen fiber bundles, and wherein the winding step comprises winding the plurality of multiple-fiber synthetic collagen fiber bundles substantially concurrently about the support member.

26. A method according to claim 1, wherein the winding step is carried out so that the at least one collagen fiber is wound at a substantially constant pitch for the first pitch and/or the second pitch for at least a major portion of a length thereof.

27. A method according to claim 1, wherein the winding step is carried out so that the winding of at least one layer of the at least one collagen fiber has a varying pitch for the first pitch and/or the second pitch over a length thereof.

28. A method of manufacturing a medical construct, comprising:
    winding at least one collagen fiber a number of revolutions about a length of a support member having a long axis, the winding having at least one defined pitch and/or fiber angle relative to the long axis of the support member to form the construct;
    placing a liquid or gel comprising soluble collagen onto the at least one wound collagen fiber during or after the winding step so that the construct is wetted and/or so that the outer surface is covered in a collagen film when the soluble collagen is dry,
    wherein the soluble collagen is an extruded gel of soluble collagen having a collagen concentration of between about 0.1% to about 4% weight per volume, and wherein a collagen fiber of the at least one collagen fiber (dry) has a diameter of between about 0.05 mm to about 0.2 mm (average).

29. A method according to claim 1, wherein the at least one collagen fiber is uncross-linked during the winding step.

30. A method according to claim 1, wherein the at least one collagen fiber is cross-linked with NDGA before the winding step.

31. A method of manufacturing a medical construct, comprising:
    winding at least one collagen fiber a number of revolutions about a length of a support member having a long axis, the winding having at least one defined pitch and/or fiber angle relative to the long axis of the support member to form the construct; and
    removing the support member after cross-linking the at least one collagen fiber while the wound at least one collagen fiber is held on the support member.

32. A method of manufacturing a medical construct, comprising:
    winding at least one collagen fiber a number of revolutions about a length of a support member having a long axis, the winding having at least one defined pitch and/or fiber angle relative to the long axis of the support member to form the construct,
    wherein the construct is a nerve guide, and wherein the nerve guide has sufficient strength and elasticity to, in use, withstand buckling and to be able to bend and to elastically return to its original shape after bending to inhibit occlusive pressures or restrictions on a nerve.

33. A method according to claim 1, wherein the support member is flat.

* * * * *